United States Patent
Hird et al.

(10) Patent No.: US 8,198,505 B2
(45) Date of Patent: Jun. 12, 2012

(54) DISPOSABLE ABSORBENT ARTICLES COMPRISING NON-BIOPERSISTENT INORGANIC VITREOUS MICROFIBERS

(75) Inventors: Bryn Hird, Colerain Township, OH (US); Robert Earl Magness, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 929 days.

(21) Appl. No.: 11/485,202

(22) Filed: Jul. 12, 2006

(65) Prior Publication Data
US 2008/0015531 A1    Jan. 17, 2008

(51) Int. Cl.
*A61F 13/15* (2006.01)
*A61F 13/20* (2006.01)

(52) U.S. Cl. .................. 604/367; 604/365; 604/378

(58) Field of Classification Search .............. 604/365, 604/367, 369, 370, 372, 375
See application file for complete search history.

(56) References Cited

U.S. PATENT DOCUMENTS

| | | | |
|---|---|---|---|
| 2,571,025 A | 10/1951 | Fletcher | |
| 3,525,338 A | 8/1970 | Bernardin | |
| 4,081,301 A | 3/1978 | Buell | |
| 4,312,952 A | 1/1982 | Carbol | |
| 4,468,428 A | 8/1984 | Early et al. | |
| 4,515,595 A | 5/1985 | Kievit et al. | |
| 4,695,278 A | 9/1987 | Lawson | |
| 4,748,977 A | 6/1988 | Guyot et al. | |
| 4,767,431 A | 8/1988 | Lewis et al. | |
| 4,795,454 A | 1/1989 | Dragoo | |
| 4,923,454 A * | 5/1990 | Seymour et al. | 604/368 |
| 4,935,022 A | 6/1990 | Lash et al. | |
| 4,935,622 A | 6/1990 | Ikeuchi et al. | |
| 4,940,464 A | 7/1990 | Van Gompel et al. | |
| 5,092,861 A | 3/1992 | Nomura et al. | |
| 5,108,957 A | 4/1992 | Cohen et al. | |
| 5,246,433 A | 9/1993 | Hasse et al. | |
| 5,350,370 A * | 9/1994 | Jackson et al. | 604/367 |
| 5,401,693 A | 3/1995 | Bauer et al. | |
| 5,496,298 A * | 3/1996 | Kuepper et al. | 604/389 |
| 5,549,589 A | 8/1996 | Horney et al. | |
| 5,554,324 A | 9/1996 | Bernard et al. | |
| 5,569,234 A | 10/1996 | Buell et al. | |
| 5,669,894 A | 9/1997 | Goldman et al. | |

(Continued)

FOREIGN PATENT DOCUMENTS
CA    1 193 290    10/1985
(Continued)

OTHER PUBLICATIONS

"Glass Fiber Dissolution in a Physiological Saline Solution", Russell M. Potter et al.

(Continued)

*Primary Examiner* — Michele M Kidwell
(74) *Attorney, Agent, or Firm* — Laura L. Whitmer; Abbey A. Lopez (57) ABSTRACT

An absorbent article having a distribution member comprising non-biopersistent inorganic vitreous microfibers. The microfibers have an average effective diameter between about 0.1 micron and about 6 microns and are arranged in a fibrous assembly having a basis weight between about 40 g/m² and about 350 g/m² and a density between about 0.04 g/m³ and about 0,25 g/m³. In preferred embodiments, the fibrous assembly can vertically wick a 0.9% saline solution to a height of 5 cm in less than about 5 minutes.

15 Claims, 5 Drawing Sheets

U.S. PATENT DOCUMENTS

| | | | |
|---|---|---|---|
| 5,827,253 A | 10/1998 | Young et al. | |
| 5,830,604 A | 11/1998 | Singleton et al. | |
| 5,843,055 A | 12/1998 | Seger | |
| 5,897,545 A | 4/1999 | Kline et al. | |
| 5,935,886 A * | 8/1999 | Jensen et al. | 501/36 |
| 5,945,360 A * | 8/1999 | Harding et al. | 501/36 |
| 5,957,908 A | 9/1999 | Kline et al. | |
| 6,015,935 A | 1/2000 | LaVon et al. | |
| 6,083,210 A | 7/2000 | Young et al. | |
| 6,107,538 A * | 8/2000 | Young et al. | 604/369 |
| 6,120,487 A | 9/2000 | Ashton | |
| 6,120,489 A | 9/2000 | Johnson et al. | |
| 6,227,009 B1 | 5/2001 | Cusick et al. | |
| 6,261,335 B1 | 7/2001 | Kern et al. | |
| 6,372,953 B1 | 4/2002 | Young et al. | |
| 6,551,295 B1 | 4/2003 | Schmidt et al. | |
| 6,570,057 B1 | 5/2003 | Schmidt et al. | |
| 6,590,136 B1 | 7/2003 | Young et al. | |
| 6,766,817 B2 | 7/2004 | da Silva | |
| 6,849,665 B2 | 2/2005 | Frenz et al. | |
| 6,932,800 B2 | 8/2005 | LaVon et al. | |
| 6,989,005 B1 | 1/2006 | LaVon et al. | |
| 6,989,006 B2 | 1/2006 | LaVon et al. | |
| 7,159,805 B2 * | 1/2007 | Reher et al. | 241/30 |
| 2002/0091368 A1 | 7/2002 | LaVon et al. | |
| 2003/0015003 A1 | 1/2003 | Fisler et al. | |
| 2003/0199844 A1 | 10/2003 | LaVon et al. | |
| 2003/0233082 A1 | 12/2003 | Kline et al. | |
| 2004/0024379 A1 | 2/2004 | LaVon et al. | |
| 2004/0030314 A1 | 2/2004 | LaVon et al. | |
| 2005/0085369 A1 | 4/2005 | Jensen | |
| 2006/0127498 A1 * | 6/2006 | Sugiura | 424/618 |
| 2006/0206088 A1 * | 9/2006 | Lavon et al. | 604/385.14 |
| 2006/0229582 A1 | 10/2006 | LaVon | |
| 2007/0016153 A1 * | 1/2007 | Hird et al. | 604/367 |
| 2007/0225669 A1 * | 9/2007 | Dyer | 604/369 |

FOREIGN PATENT DOCUMENTS

| | | |
|---|---|---|
| EP | 0 095 917 A1 | 12/1983 |
| EP | 1 048 625 B1 | 1/2004 |
| FR | 2 682 556 | 4/1993 |
| WO | WO 99/45878 A1 | 9/1999 |
| WO | WO 99/47091 A1 | 9/1999 |
| WO | WO 2007/007286 A1 | 1/2007 |
| WO | WO 2007/110830 A2 | 10/2007 |

OTHER PUBLICATIONS

Russell M. Potter, A method for determination of in-vitro fiber dissolution rate by direct optical measurement of diameter decrease; http://fiberscience.owenscorning.com/ompaper/ompaper.html.

IARC Monographs on the Evaluation of Carcinogenic Risks to Humans; http://www-cie.iarc.fr/htdocs/announcements/vol81.htm.

* cited by examiner

DISPOSABLE ABSORBENT ARTICLES COMPRISING NON-BIOPERSISTENT INORGANIC VITREOUS MICROFIBERS

FIELD OF THE INVENTION

This application relates to disposable absorbent articles comprising non-biopersistent inorganic vitreous microfibers. This application further relates to members for distributing body liquids such as urine and menses where the members comprise non-biopersistent inorganic vitreous microfibers. This application particularly relates to disposable absorbent articles comprising members for distributing body fluids, where the members comprise non-biopersistent inorganic vitreous microfibers.

BACKGROUND OF THE INVENTION

Highly absorbent articles such as disposable diapers, adult incontinence pads and briefs, and catamenial products such as sanitary napkins, are the subject of substantial commercial interest. Highly desired characteristics of such products are thinness and sustained fit. For example, thin diapers fit better under clothing, provide more freedom of movement to the wearer, and are less noticeable than bulky diapers.

The ability to provide thinner absorbent articles such as diapers has been contingent on the ability to develop relatively thin absorbent cores or structures that can sequester large quantities of discharged body liquids, in particular urine. Upon the discharge of a gush of body fluid into an absorbent article, three distinct mechanisms for handling the fluid may be considered; viz. acquisition, distribution, and storage. Cores in absorbent articles often comprise layers or members to perform these functions. A member may perform one or more functions. For example, a member comprising cellulose fibers and superabsorbent particles may perform fluid distribution and storage as well as some fluid acquisition.

Fluid distribution within an absorbent article is important because absorption of relatively large quantities of fluid in the discharge region of an absorbent article (i.e., the crotch region) tends to increase the bulkiness and weight of this region considerably. This bulk between the legs leads to decreased comfort for the wearer. Further, the localized weight in the discharge region, together with the relatively large dimensional changes as fluids are absorbed, can cause the crotch of the article to sag. This, in turn, can lead to gaps between any leg cuffs or leakage barriers and the skin of the wearer, especially in the discharge region. This can facilitate leakage of fluid from the product, particularly upon subsequent gushes of fluid. Transport or distribution of liquid from the discharge region to the rear and/or front of the article ameliorates localization of the bulk and weight of the fluid. If the need to provide substantial storage capacity in the crotch region is reduced, the resulting design flexibility can enable products which provide enhanced sustained fit and comfort, and can reduce the incidence of leakage.

Fluid distribution from the discharge region to the back and/or front of the article often requires transport against gravity. For example, transport of fluid from the crotch area to the waist area of a diaper with the wearer in a standing position can require the fluid to rise up to 20 cm against gravity, depending on the size and design of the diaper. This distribution of fluid against gravity is typically accomplished via a wicking mechanism. More specifically, the fluid is transported by means of capillary forces within a porous matrix. Typically, the porous matrix comprises cellulose fibers, although other fibers or porous media (e.g., foams) are known in the art.

In addition to wicking the fluid against gravity, the capillary forces in the distribution member must be sufficient to dewater any fluid acquisition materials to the desired level of residual moisture. The level of residual moisture in the regions of the absorbent core closest to the wearer's skin tend to have a significant effect on the dryness of the skin, and/or the wearer's perception of how well the article absorbs fluid.

The rate at which fluid is transported from the discharge region to other regions of an absorbent article is also of critical importance. The propensity for free fluid to leak from an absorbent article is reduced if the fluid is transported to the location where it will be stored (i.e., typically absorbed osmotically by a superabsorbent polymer) as rapidly as possible. A relatively high rate of fluid transport for a given cross-sectional area of the member (i.e., flux) allows the absorbent article comprising the member to have a narrow crotch region while achieving the desired levels of performance in terms of leakage and skin dryness. A narrow crotch facilitates good fit and wearer comfort.

Hydrophilic porous structures with relatively small pores tend to facilitate high capillary forces which enable aqueous fluids to be wicked to relatively high heights against gravity. However, small pores also tend to diminish the permeability of the structure to fluid, so the rate of fluid transport through the structure is impaired. A tradeoff between wicking height and wicking rate typically exists for a given class of porous materials with specific surface properties and fiber (or strut) dimensions.

Amongst other factors, surface tension of the fluid is important in governing the capillary forces responsible for fluid distribution within a porous structure such as an absorbent article. The surface tension of the fluid can be lowered by any surfactants present in the absorbent member. For example, some of the fibrous and foam structures of the art are treated with surfactants to enhance their hydrophilicity. Such surfactants can reduce the surface tension of absorbed fluids undesirably. Capillary forces tend to be lower with fluids having relatively low surface tension. Fluids with low surface tension can be also difficult to desorb from porous structures (e.g., acquisition members). Furthermore, fluids with low surface tension tend to wet surfaces such as skin more readily than fluids with relatively high surface tension, and tend to be more prone to leak through small gaps or openings such as pinholes or pores in the backsheet or cuffs of an absorbent article. Thus, it is desirable for the distribution member (and other components) to lower the surface tension of the fluid as little as possible, and preferably not at all.

Another desired property of the fluid distribution member is its ability to maintain adequate fluid distribution and wicking rate when subjected to forces typically encountered during normal use of an absorbent article. In order to wick aqueous fluids effectively, it is necessary for the material comprising the porous matrix of the distribution member to be hydrophilic. Hydrophilic porous materials conventionally used in diaper cores (e.g., cellulosic fibers) tend to absorb some water when wetted with an aqueous fluid. This absorbed moisture tends to plasticize the material, thereby softening or weakening it, making is susceptible to collapse under the mechanical and gravitational forces exerted on the member during normal use of the absorbent article. Collapse of the structure can lead to undesirable effects, including changes in the pore size, capillary forces and wicking properties of the member. The presence of any superabsorbent particles within the structure also can have an adverse effect on the fluid distribution capability of the member. Superabsorbent particles tend to swell and soften significantly as they absorb fluid. This can disrupt the structure and impede the flow of fluid through the member.

Although it is advantageous for the distribution member to resist collapse during use, it is desirable for it to remain non-rigid, i.e., relatively flexible and soft. This allows the absorbent article comprising the member to conform to the body of the wearer, thus providing good fit and comfort.

Yet another desired attribute of the distribution member is resilience and/or resistance to stress relaxation. Absorbent articles are often subjected to some level of compression during packaging in order to facilitate a relatively compact package. This reduces shipping, handling and storage costs relating to the finished product, and enhances consumer convenience. The forces applied to the articles in order to compress them for packaging may also cause the distribution member within the articles to become compressed. Upon removal of an absorbent article from the package, it is desirable for the acquisition member to re-expand to its original dimensions in order to provide the intended fluid handling properties.

It is further desirable that the materials comprising the fluid distribution member should be non-hazardous, non-irritating, free from malodors, and preferably white in color.

Accordingly, it would be desirable to provide a fluid distribution member for an absorbent article, where the fluid distribution member has the following attributes:

1) Capillary forces sufficient to distribute fluid throughout the member and to dewater any acquisition members to the desired degree during use of the absorbent article
2) Fluid distribution at a rate sufficient to prevent leakage
3) Does not lower the surface tension of fluid excessively
4) Resilient and resistant to stress relaxation
5) Soft and flexible
6) Non-hazardous and non-irritating
7) Free from malodors
8) Preferably white in color Surprisingly, it has been found that distribution members comprising certain non-biopersistent inorganic vitreous microfibers are capable of having all of these attributes.

Inorganic vitreous microfibers have been disclosed as being useful in disposable absorbent products for a variety of purposes. However, none meet all of the above desired attributes for a distribution member. For example, U.S. Pat. No. 3,525,338 discloses the use of certain elements made up of glass microfibers for fluid storage where the glass microfibers have an average diameter of less than about 0.75 microns. U.S. Pat. No. 4,748,977, discloses certain hygienic products comprising a layer of interlaced mineral fibers whose specific surface area is at least 0.25 $m^2/g$ and whose average diameter is under 5 microns. U.S. Pat. No. 6,590,136 discloses certain storage absorbent members comprising glass microfibers. However, the art has failed to recognize the need for such fibers used in disposable absorbent articles to be non-biopersistent.

Distribution members made from materials such as foams have also been disclosed. For example, U.S. Pat. No. 6,013,589 discloses certain foams derived from high internal phase emulsions. However, none of the prior art materials meet all of the above desired attributes for a distribution member.

SUMMARY OF THE INVENTION

The present invention relates to disposable absorbent articles with cores comprising non-biopersistent inorganic vitreous microfibers. The present invention further relates to members for distributing body liquids such as urine and menses where the members comprise non-biopersistent inorganic vitreous microfibers. The microfibers have an average effective diameter between about 0.1 microns and about 6 microns and are in the form of a fibrous assembly with a density between about 0.04 $g/m^3$ and about 0.25 $g/m^3$ and a basis weight between about 40 $g/m^2$ and about 350 $g/m^2$.

DETAILED DESCRIPTION OF THE INVENTION

I. Definitions

As referred to herein, "disposable" absorbent articles are those which are intended to be discarded after a limited number of uses, frequently a single use (i.e., the original absorbent article as a whole is not intended to be laundered or reused as an absorbent article, although certain materials or portions of the absorbent article may be recycled, reused, or composted). Certain disposable absorbent articles may be temporarily restored to substantially full functionality through the use of removable/replaceable components but the article is nevertheless considered to be disposable because the entire article is intended to be discarded after a limited number of uses.

As used herein, the term "diaper" refers to a garment generally worn by infants and incontinent persons that is worn about the lower torso of the wearer. It should be understood, however, that the present invention is also applicable not only to diapers as defined above but also to other absorbent articles such as incontinent briefs, incontinent pads, training pants, diaper inserts, catamenial pads, sanitary napkins, tampons, bandages, facial tissues, paper towels, and the like.

As used herein, the term "body liquids" includes, but is not limited to, urine, menses, vaginal discharges, blood, sweat and feces.

As used herein, the term "absorbent core" refers to the component of the absorbent article that is primarily responsible for liquid handling properties of the article, including acquiring, distributing and storing body liquids. As such, the absorbent core typically does not include the topsheet or backsheet of the absorbent article.

As used herein, the term "absorbent member" refers to a component of the absorbent core that typically provides one or more liquid handling functions, i.e., fluid acquisition, distribution or storage. The absorbent member can comprise the entire absorbent core or only a portion of the absorbent core, i.e., the absorbent core can comprise one or more absorbent members. The "fluid distribution member" or "distribution member" is the component(s) of the absorbent core that functions primarily to distribute absorbed liquids. As discussed above, the fluid distribution member may also function to acquire fluid.

As used herein the term "removable" refers to a component that can be removed from the absorbent article (with or without removing the article from the wearer) without causing damage to the article.

A "replaceable" component is one that may be inserted into the absorbent article without damaging the article so as to again provide the functionality of a component that was removed. The removed component is typically soiled by urine, and is replaced by another unsoiled component, but the original component may be re-inserted as desired if unsoiled.

As used herein, the term "superabsorbent" refers to a material capable of absorbing at least ten times its dry weight of a 0.9% saline solution at 25° C. Superabsorbent polymers absorb fluid via an osmotic mechanism to form a gel.

As used herein, the term "microfibers" refers to fibers with an average effective diameter of from about 0.1 micron to about 6 microns and an aspect ratio of at least about 100, where the aspect ratio of the microfiber is its contour length divided by its average effective diameter. Long microfibers can have aspect ratios which exceed $1\times10^{12}$. The microfiber may be of any configuration, including but not limited to straight, curled, kinked, crimped, and combinations thereof. The cross sectional area of the microfiber orthogonal to its contour length at any point may have any geometric shape, including but not limited to circular (round), square, flat, oval, star-shaped, irregular, and combinations thereof. For fibers with a non-circular cross section, the effective diameter is the diameter of the circle having a cross sectional area equal to that of the fiber. Microfibers may comprise any material, including but not limited to natural polymers, synthetic polymers, minerals, glass, ceramics, metals, vegetable matter, animal matter, carbon, and combinations thereof. A sample of microfibers with an average effective diameter between 0.1 and 6 microns may contain individual fibers with diameters greater than 6 microns and/or individual fibers with diameters less than 0.1 micron. A member comprising such a material is within the scope of the current invention as long as the average effective diameter is between 0.1 and 6 microns.

As used herein, the term "inorganic" refers to a material which is not organic in nature. As used herein, the term "organic" refers to compounds of carbon.

As used herein, the term "vitreous" refers to a material which is substantially non-crystalline (i.e., contains more than 90% amorphous material, preferably more than 99% amorphous material) and which is glassy at room temperature.

As used herein, an inorganic vitreous microfiber is "non-biopersistent" if its in vitro dissolution rate, $k_{dis}$, is equal to or greater than 100 ng/cm$^2$/hr when measured according to the test method described below.

As used herein, the term "layer" refers to an absorbent member whose primary dimension is X-Y, i.e., along its length and width. It should be understood that the term layer is not necessarily limited to single layers or sheets of material. Thus the layer may comprise laminates or combinations of several sheets or webs of the requisite type of materials. Accordingly, the term "layer" includes the terms "layers" and "layered."

As used herein, the term "X-Y dimension" refers to the plane orthogonal to the thickness of the member, core or article. The X-Y dimension usually corresponds to the length and width, respectively, of the member, core or article when the article is laid flat, with the X dimension being the longest dimension.

As used herein, the term "Z-dimension" refers to the dimension orthogonal to the length and width of the member, core or article. The Z-dimension usually corresponds to the thickness of the member, core or article.

As used herein, the terms "region(s)" or "zone(s)" refer to portions or sections of the absorbent article or component thereof.

As used herein, the term "flexible" refers to materials which are compliant and which will readily conform to the general shape and contours of the wearer's body.

For purposes of this invention, it should also be understood that the term "upper" refers to absorbent members, such as layers, that are nearest to the wearer of the absorbent article, and typically are relatively proximate the topsheet of an absorbent article; conversely, the term "lower" refers to absorbent members that are furthermost away from the wearer of the absorbent article and typically are more proximate the backsheet.

As used herein, the term "comprising" means various components, members, steps and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios and proportions used herein are by weight unless otherwise specified.

II. Uses of Distribution Materials of the Present Invention

A. General

Distribution materials according to the present invention are broadly useful in absorbent cores of disposable diapers, as well as other absorbent articles. These materials can also be employed in other absorbent articles, especially when there is a need to wick liquid to some height against the force of gravity.

B. Absorbent Articles

Figure 1:
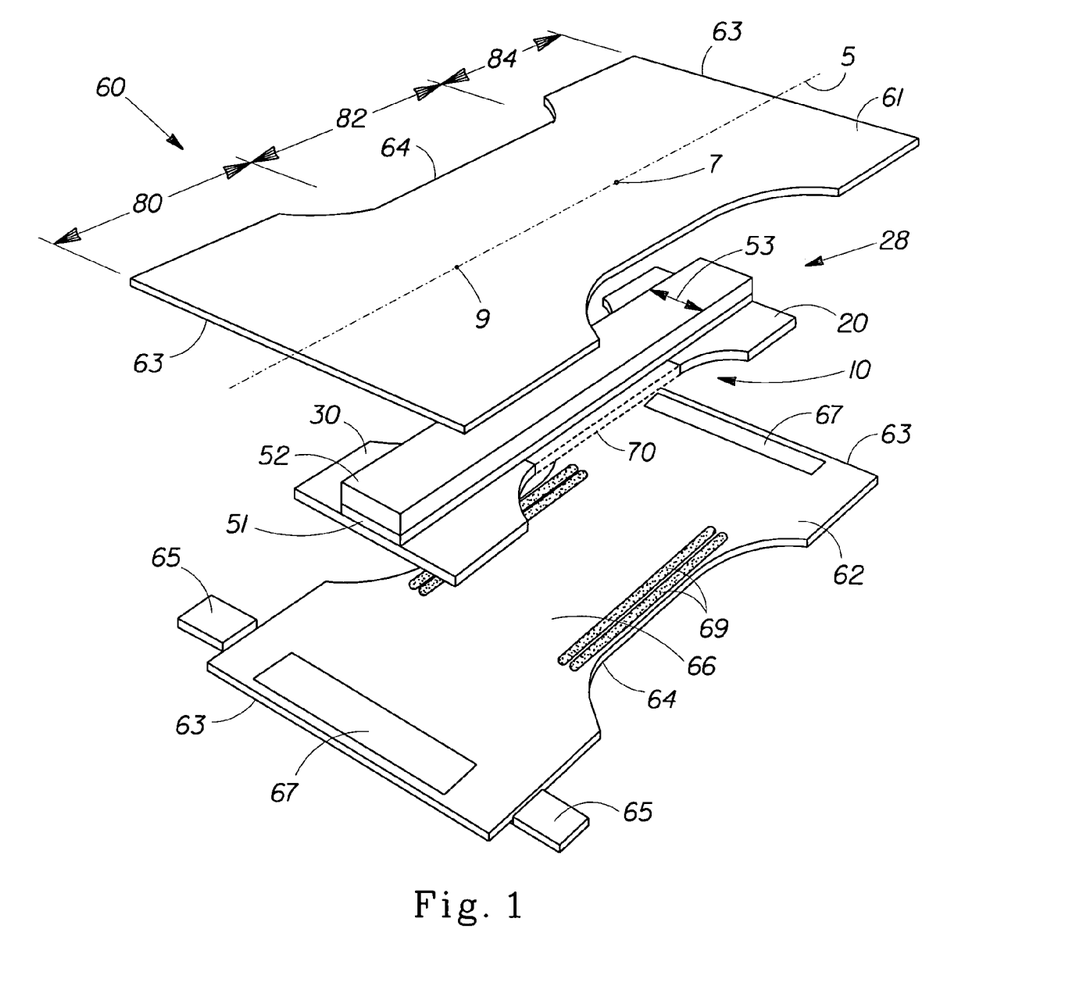
FIG. 1 of the drawings is an exploded view of a diaper having an absorbent core which comprises a fluid distribution member of the present invention comprising non-biopersistent inorganic vitreous microfibers.

FIG. 1 shows a preferred embodiment of a diaper 60 in which the topsheet 61 and the backsheet 62 are co-extensive and have length and width dimensions generally larger than those of the absorbent core 28. The topsheet 61 is joined with and superimposed on the backsheet 62 thereby forming the periphery of the diaper 60. The periphery defines the outer perimeter or the edges of the diaper 60. Diaper 60 also has crotch region 82, front waist region 84 and rear waist region 80. As used herein, these regions are defined as follows. The X-direction length ($L_X$) of the diaper 60 is measured along the longitudinal centerline 5 of the diaper equidistant from the longitudinal edges with the diaper laid flat. The length of the diaper $L_X$ is divided into three segments of equal length by two points 7 and 9, with 7 closer to the front of the diaper than 9. The front waist region 84 is defined as the region of the diaper forward of the Y-Z plane which intersects centerline 5 at point 7. The rear waist region 80 is defined as the region of the diaper to the rear of the Y-Z plane which intersects centerline 5 at point 9. The crotch region 82 is defined as the region of the diaper between the front waist region 86 and the rear waist region 80.

The topsheet 61 is compliant, soft feeling, and non-irritating to the wearer's skin. Further, the topsheet 61 is liquid pervious permitting liquids to readily penetrate through its thickness. A suitable topsheet 61 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. In one embodiment, the topsheet 61 is made of a hydrophobic material to isolate the wearer's skin from liquids in the absorbent core 10. Preferably the topsheet comprises a means to adjust hydrophilicity of the material.

A suitable topsheet is a nonwoven material made using means well known to those skilled in the fabrics art. Preferably, the topsheet 61 has a basis weight from about 10 to about 25 g/m$^2$, a minimum dry tensile strength of at least about 150 g/cm in the machine direction and a strikethrough of less than about 3 seconds according to European Disposables and Nonwovens Association standard method 150.4-99. One suitable topsheet 61 comprises a polypropylene spunbonded nonwoven comprises fibers of less than 3 denier having a basis weight of about 18 g/m$^2$ as is available from BBA Fiberweb of Simpsonville, S.C.

The backsheet 62 prevents the exudates absorbed and contained in the absorbent core 10 from wetting articles which contact the diaper 60 such as bed sheets and garments. The backsheet 62 is preferably manufactured from a thin polymer film. In one preferred embodiment the film comprising backsheet 62 is impervious to liquids. Typically, the backsheet 62 comprises a layer of polyethylene film having a basis weight between about 10 g/m$^2$ and about 30 g/m$^2$, although other flexible, liquid impervious materials can be used. Preferably, the film is breathable (e.g., via micropores) so as to permit vapors to escape from the diaper 60 while still preventing exudates from passing through the backsheet 62. Particularly preferred backsheet materials have a nonwoven laminated to the film layer so as to make backsheet 62 more "cloth-like". Such a nonwoven layer may comprise a nonwoven material (e.g., one having a spunbonded or other suitable structure) with a basis weight between about 15 g/m$^2$ and about 25 g/m$^2$. Suitable materials for use as backsheet 62 are available form Clopay Plastic Products Company of Mason, Ohio.

The size of the backsheet 62 is dictated by the size of the absorbent core 28 and the exact diaper design selected. In one preferred embodiment, the backsheet 62 has a modified hourglass-shape extending beyond the absorbent core 28 a minimum distance of at least about 1.3 centimeters to at least about 2.5 centimeters (about 0.5 to about 1.0 inch) around the entire diaper periphery.

The topsheet 61 and the backsheet 62 are joined together in any suitable manner. As used herein, the term "joined" encompasses configurations whereby the topsheet 61 is directly joined to the backsheet 62 by affixing the topsheet 61 directly to the backsheet 62, and configurations whereby the topsheet 61 is indirectly joined to the backsheet 62 by affixing the topsheet 61 to intermediate members which in turn are affixed to the backsheet 62. In a preferred embodiment, the topsheet 61 and the backsheet 62 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 61 to the backsheet 62.

The diaper 60 may also include a fastening system 65. The fastening system 65 preferably maintains diaper 60 in a configuration so as to provide lateral tensions about the circumference of the diaper 60 to hold the diaper 60 on the wearer. The fastening system 65 preferably comprises a fastener such as tape tabs, hook and loop fastening components, interlocking fasteners such as "tabs and slots", buckles, buttons, snaps, and/or cohesive fastening components, although any other known fastening means are generally acceptable.

Elastic members 69 are disposed adjacent the periphery of the diaper 60, preferably along each longitudinal edge 64, so that the elastic members tend to draw and hold the diaper 60 against the legs of the wearer. Additionally, elastic members 67 can be disposed adjacent either or both of the waistband regions 63 of the diaper 60 to provide a waistband as well as or rather than leg cuffs. For example, a suitable waistband is disclosed in U.S. Pat. No. 4,515,595. In addition, a method and apparatus suitable for manufacturing a disposable diaper having elastically contractible elastic members is described in U.S. Pat. No. 4,081,301. Additional elastic features (not shown) may be disposed inboard of the longitudinal edges 64 to provide additional protection against leakage. Such inboard features are described in U.S. Pat. Nos. 4,695,278 and 4,795,454.

The elastic members may be secured to the diaper 60 in an elastically contractible condition so that in a normally unrestrained configuration, the elastic members effectively contract or gather the diaper 60. The elastic members can be secured in an elastically contractible condition in at least two ways. For example, the elastic members can be stretched and secured while the diaper 60 is in an uncontracted condition. Alternatively, the diaper 60 can be contracted, for example, by pleating, and the elastic members secured and connected to the diaper 60 while the elastic members are in their unrelaxed or unstretched condition. The elastic members may extend along a portion of the length of the diaper 60. Alternatively, the elastic members can extend the entire length of the diaper 60, or any other length suitable to provide an elastically contractible line. The length of the elastic members is dictated by the diaper design.

In alternative embodiments (not shown), the article may be preformed by the manufacturer by joining opposing portions of the longitudinal edges 64 that lie adjacent to the end edges 63 to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433; 5,569,234; 6,120,487; 6,120,489; 4,940,464; 5,092,861; 5,897,545; 5,957,908 and in U.S. Pat. Application Publication 2003/0233082A1.

In use, the diaper 60 is applied to a wearer by positioning one waistband region under the wearer's back, and drawing the remainder of the diaper 60 between the wearer's legs so that the other waistband region is positioned across the front of the wearer. The fastening system 65 is then secured preferably to outwardly facing areas of the diaper 60.

When used as an absorbent core in a disposable diaper 60, a preferred embodiment of the core 28 according to the present invention is positioned such that an acquisition member 52 is in liquid communication with topsheet 61, and serves to quickly acquire and partition body exudates from the wearer's body to distribution member 51. Adhesive bonding of acquisition member 52 to topsheet 61 may enhance the liquid communication by providing interfacial bonding and preventing topsheet separation from impeding liquid flow. A distribution member 51 of the present invention moves liquid in the X and Y dimensions of the core 28 and the liquid is subsequently absorbed by the liquid storage component, shown generally as 10. While components 52 and 51 are shown generally as being rectilinear and of equal size, other shapes and size relationships may be utilized. As shown, the generally rectilinear components have a width 53 corresponding to a suitable width for the crotch area 66 of a disposable diaper. As well, the length of the respective core components may be varied to provide a suitable fit for various wearer sizes.

As is shown in FIG. 1, storage component 10 can comprise two separate storage components 20 and 30 such that there is no absorbent storage member element located in the liquid discharge region of the diaper. Because such an absorbent core 10 has little or no liquid storage material in the center of the core (corresponding to the crotch or liquid discharge region of the core), articles containing such cores may provide improved fit and wearer comfort both when the article is dry and after it has received several loadings of body liquid (it should be recognized that the distribution member 51 may have significant storage capacity and will contain liquid, at least until the fluid is absorbed by another material such as a porous member with relatively high capillary suction, or an osmotic absorbent such as a superabsorbent polymer, or combinations thereof). See, for example, U.S. Pat. Nos. 6,083,210, 6,015,935, and 5,827,253.

Figure 2A:
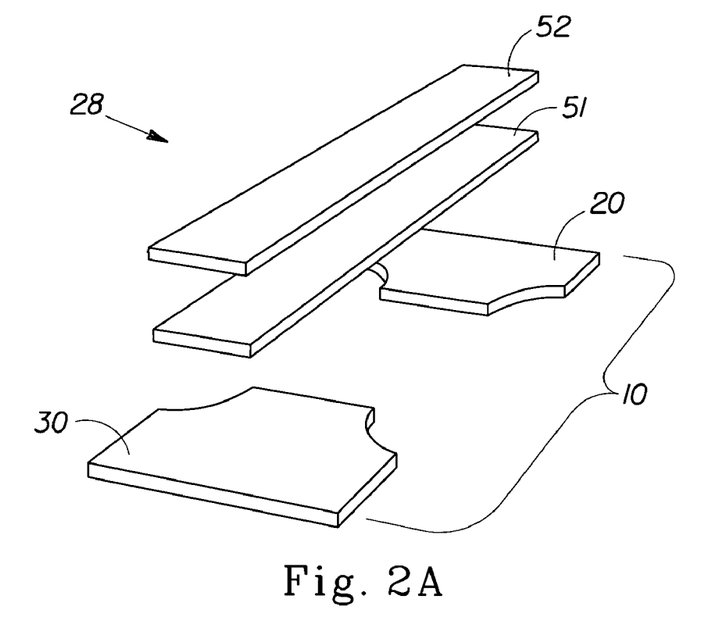
FIG. 2A of the drawings is a blown-apart view of a representative multi-layer core for inclusion in a diaper such as that shown in FIG. 1.

FIG. 2A depicts a blown-apart view of absorbent core 28 having two separated components 20 and 30, each of which consists of a storage absorbent member that will absorb fluid from distribution member 51. Front panel 20 generally corresponds to the portion of the disposable diaper worn in the front of the wearer (i.e., in front waist region 84). Similarly, the back panel 30 corresponds to the portion of the disposable diaper worn in the back of the wearer (i.e., in back waist region 80).

Figure 2B:
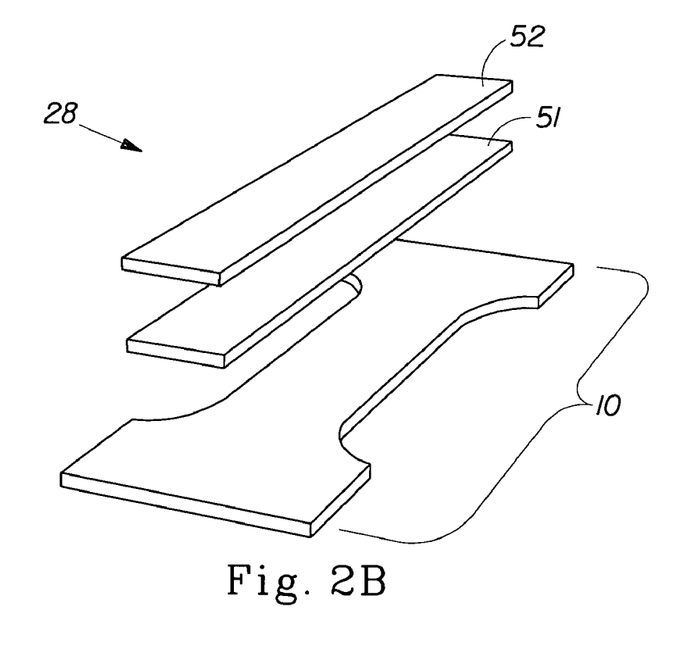
FIG. 2B of the drawings is a blown-apart view of another representative multi-layer core for inclusion in a diaper shown such as that shown in FIG. 1.

Alternatively, storage component 10 may be a unitary layer or layers of storage material (i.e., where the dashed lines 70 in FIG. 1 indicate that storage component 10 is included in the liquid discharge region of the article). Such an embodiment of an absorbent core 28 is depicted in FIG. 2B.

In one embodiment, acquisition member 52 will be a liquid handling layer, positioned in the liquid discharge region of the wearer of the article, in the form of a high loft nonwoven. A preferred material of this type is a carded, resin bonded polyester nonwoven material having a basis weight of about 60 g/m$^2$ as is available from BBA Fiberweb of Simpsonville, SC. Alternatively, acquisition member 52 may be in the form of a layer of modified cellulosic fibers, e.g., stiffened curled cellulosic fibers, and, optionally, up to about 10% by weight of this layer of superabsorbent material. The modified cellulosic fibers used in the liquid acquisition member 52 of such an embodiment are preferably wood pulp fibers that have been stiffened and curled by means of chemical and/or thermal treatment. Such modified cellulosic fibers are of the same type as are employed in the absorbent articles described in U.S. Pat. No. 4,935,022. In other embodiments, acquisition member 52 may comprise blends of synthetic fibers, semi-synthetic fibers and natural fibers as desired. A preferred blend of this type is a carded, through air bonded 50/50 blend of staple length 4.2 denier rayon fibers and 6.0 denier polyester fibers having a basis weight of about 250 g/m$^2$. As used herein, the term "staple length fibers" refers to those fibers having a length of at least about 15.9 mm (0.62 inches).

Distribution members 51 of the present invention comprise non-biopersistent inorganic vitreous microfiber material (described in detail below). Because these members are effective and efficient at distributing aqueous liquids, they are particularly useful as the liquid distribution component of an absorbent core 28 that benefits from such liquid movement.

Such liquid movement capability is especially useful in a preferred embodiment of absorbent core 28 where not more than about 40% of the total superabsorbent polymer present in absorbent core 28 is located in crotch region 82. Such cores are designed so that most of the absorbed liquid is stored away from crotch region 82 in one or both of end regions 80, 84. The weight of superabsorbent polymer in each region 80, 82, 84 may be measured by cutting diaper 60 perpendicular to longitudinal centerline 5 to separate crotch region 82 from front and rear waist regions 80 and 84. The amount of superabsorbent polymer in each region is then determined using methods known to the art (e.g., titration). The percent superabsorbent polymer in crotch region 82 is defined as the quantity of superabsorbent polymer therein divided by the total amount of superabsorbent in core 28 multiplied by 100.

By designing a crotch region 82 to have a relatively low absorbent capacity, the crotch region 82 can be made narrow. Suitably, for infant diapers, crotch regions of this type have a width at the narrowest point of less than about 7 cm, preferably less than about 6 cm, more preferably less than about 5 cm. As described above, a narrow crotch facilitates good fit and comfort for the wearer of the disposable article. Such designs are described in U.S. Pat. Nos. 6,015,935 and 6,083,210.

In some embodiments according to the present invention, the distribution member of the absorbent core will be placed in a specific positional relationship with respect to the topsheet and the storage component of the absorbent core. More particularly, the distribution member 51 of the core is preferably positioned so that it is effectively located to receive discharged body liquid from the acquisition member 52 and transport such liquid to other regions of the core. Thus the distribution member 51 can span between an acquisition zone (e.g., in the crotch region) and some distal storage zone. The acquisition layer would include the crotch area and, preferably for articles to be worn by males, also the region where urination discharges occur in the front of the diaper. For a diaper, the front of the absorbent article means the portion of the absorbent article which is intended to be placed on the front of the wearer.

For diaper executions, the distribution member 51 of the core can be positioned relative to an elongated topsheet and/or the storage component such that the distribution member 51 is of sufficient length to extend to areas corresponding at least to about 50%, preferably at least about 75%, of the length of the topsheet and/or from about 50 to about 200% of the total length of the storage component(s). The distribution member 51 should have a width sufficient to receive body liquids from the acquisition layer. Generally, for infant diapers, the width of the distribution member 51 at the narrowest point in the crotch area will be less than 7 cm, preferably less than about 6 cm, more preferably less than about 5 cm The distribution member 51 can be of any desired shape consistent with comfortable fit and the sizing limitations discussed above. These shapes include, for example, hourglass-shaped, rectangular or oblong, trapezoidal, dog-bone-shaped, half-dog-bone-shaped, oval, triangular, circular, or irregularly shaped. The distribution layer can be of similar shape or differing shape from that of the storage component. The storage component of the preferred absorbent core configuration can also be of any desired shape consistent with comfortable fit including, for example, hourglass-shaped, rectangular or oblong, trapezoidal, dog-bone-shaped, half-dog-bone-shaped, oval, triangular, circular, or irregularly shaped. (The storage component need not be physically separated from the distribution member 51 or completely unattached from the distribution member 51.)

Figures 3A, 3B:
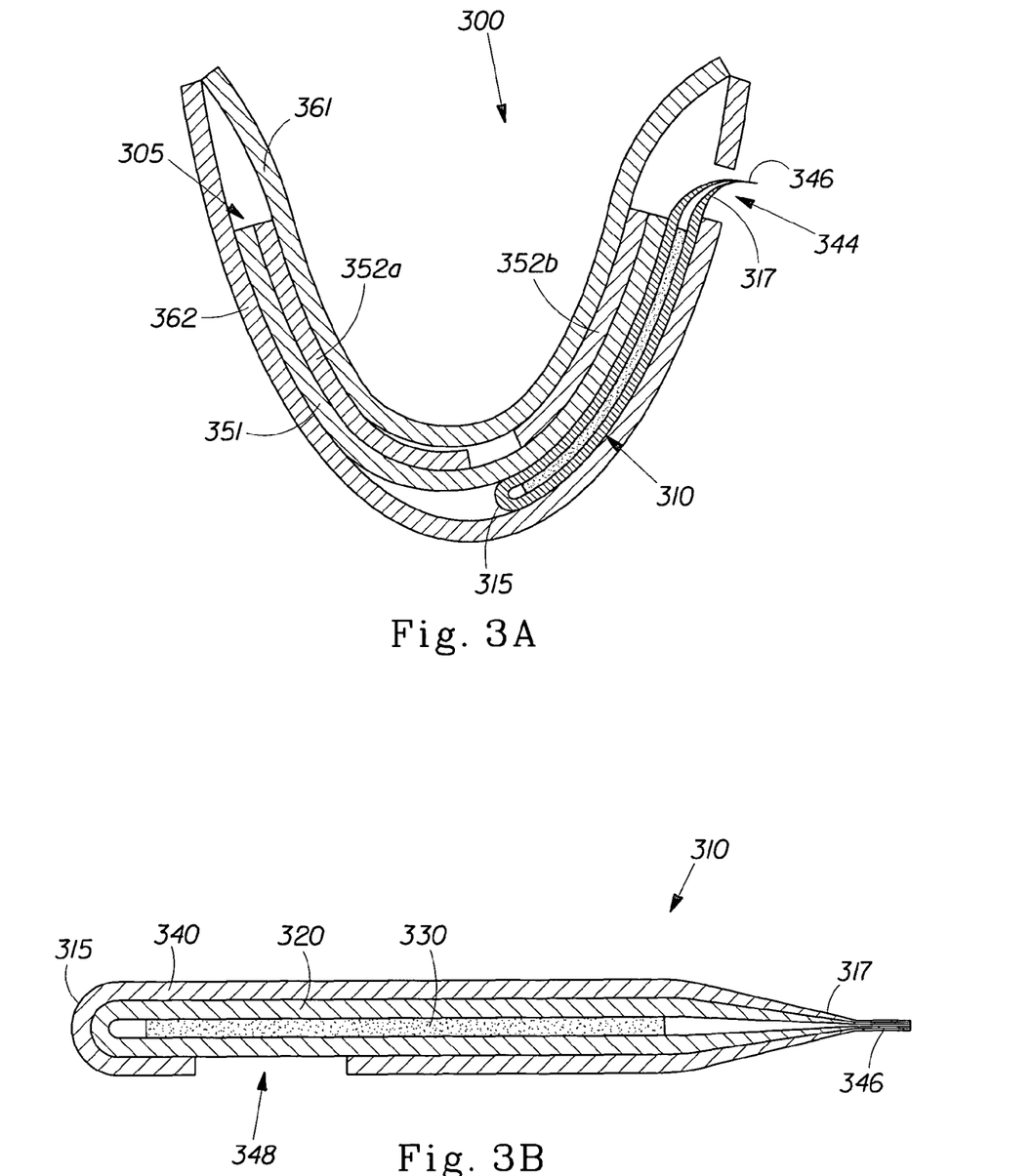
FIG. 3A is a cross sectional view of an embodiment of an absorbent article with a removable/replaceable component of the present invention comprising non-biopersistent inorganic vitreous microfibers.
FIG. 3B is an enlarged cross sectional view of the removable/replaceable component shown in FIG. 3A.
Figure 4:
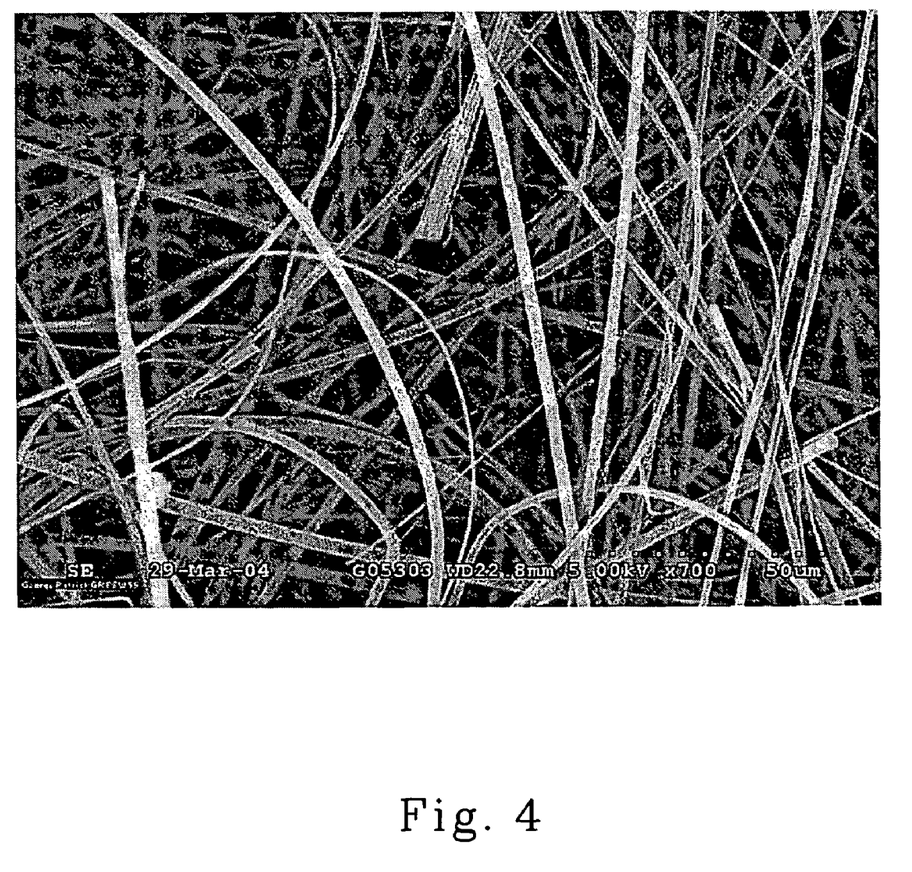
FIG. 4 is a photomicrograph (50 micron scale bar) of representative non-biopersistent inorganic vitreous microfibers having an average effective diameter of 1.8 microns.

FIGS. 3A and 3B represent an alternative embodiment of the present invention, diaper 300, which comprises a removable/replaceable core component 310. Embodiments of this type have the added benefit of not requiring a complete change of the absorbent article if the absorbent article is soiled as a result of urination only.

As can be seen most clearly in FIG. 3A, diaper 300 comprises topsheet 361 and backsheet 362 with non-removable core component 305 and removable/replaceable core component 310 disposed therebetween. Opening 344 provides access to the volume between topsheet 361 and backsheet 362 for insertion and removal of removable/replaceable core component 310. Extension 346 provides a gripping surface to aid in removal of removable/replaceable core component 310.

Non-removable core component 305 comprises acquisition member 352 (shown in FIG. 3A as two part acquisition member 352a and 352b) and fixed (i.e., non-removable) distribution member 351. Acquisition member 352 is generally in capillary liquid communication with topsheet 361 of the disposable diaper 300, thereby acting to quickly acquire and partition bodily exudates away from the wearer's body to the generally more absorptive fixed distribution member 351 and to the removable/replaceable core component 310. Adhesive bonding of acquisition member 352 to the topsheet 361 may enhance the capillary liquid communication by providing interfacial bonding and preventing topsheet separation from impeding liquid flow.

Materials suitable for acquisition member 352 and fixed distribution member 351 are generally the same materials described above for use in acquisition member 52 and distribution member 51. However, depending upon the design of diaper core 28, the fixed distribution member 351 is not necessarily required to wick fluids as high as distribution member 51 (see FIG. 1) because of the presence of a second distribution member 320 in the removable/replaceable core component 310. In particular, the fixed distribution member 351 has a capillary absorption pressure greater than the capillary desorption pressure of acquisition member 352, and a capillary desorption pressure less than or equal to the capillary absorption pressure of the removable distribution member 320, at a given moisture content. An exemplary material for use in the fixed distribution member 351 is a wet laid web comprising a blend of cellulosic fibers (particularly stiffened twisted cellulosic fibers) and a binder as described in U.S. Pat. Nos. 5,549,589 and 5,843,055. The fixed distribution member may also comprise non-biopersistent inorganic vitreous microfibers as described below.

Removable/replaceable core component 310 comprises removable distribution member 320 and superabsorbent storage material 330. One particularly preferred embodiment further comprises covering layer 340 and permeable liquid transfer region 348. Covering layer 340 substantially encapsulates the removable/replaceable core component 310. Suitably, superabsorbent material 330 is adhesively bonded to at least one face of removable distribution member 320 so as to provide readily accessible volume for osmotic storage of absorbed aqueous liquids. The removable distribution member 320 may comprise one or more layers of distribution material. In one preferred embodiment (as illustrated in FIG. 3B), the distribution material is folded lengthwise around the superabsorbent 330 to form crotch end 315 and the superabsorbent is adhesively laminated to distribution member 320. In alternative embodiments, superabsorbent material 330 may be either homogeneously distributed within the removable/replaceable core component 310, or inhomogeneously distributed. When superabsorbent material 330 is inhomogeneously distributed the distribution may provide either a higher amount of superabsorbent adjacent crotch end 315 or adjacent waist end 317 of removable/replaceable core component 310. A suitable inhomogeneous distribution having a greater amount of superabsorbent adjacent crotch end 315 of removable/replaceable core component 310 may be achieved by adhesively laminating the superabsorbent to a web of the distribution material to form a composite wherein the amount of superabsorbent is greater along the center of the web than along the edges. The web is then folded down its centerline with the superabsorbent placed on the inside of the folded composite. Core components are cut from the folded composite in the cross direction while preserving the fold. As will be recognized, the folded end of the composite forms the crotch end 315 of the finished removable/replaceable core component 310.

Transfer region 348 is provided so as to ensure that non-removable core component 305 and removable/replaceable core component 310 are in fluid communication. In some instances it may be desirable to provide an interface layer (not shown) between removable/replaceable core component 310 and overlying and underlying layers so as to reduce frictional resistance during installation and removal of removable/replaceable core component 310. When used, an interface layer should comprise a substantially hydrophilic material so as to minimally resist fluid communication between non-removable core component 305 and removable/replaceable core component 310. A suitable material for this use is a polyolefin having an ionic material grafted thereto. An exemplary material of this type comprises polypropylene having acrylic acid grafted thereto which is described in U.S. Pat. No. 5,830,604.

Superabsorbent material 330 may comprise any superabsorbent polymer as may be known to the art as suitable for absorption of aqueous liquids in a disposable absorbent article. An exemplary material of this type is the partially neutralized polyacrylic acid, ASAP 500, as is available from BASF Corporation Superabsorbents of Charlotte, N.C. Other suitable superabsorbent polymers are disclosed in U.S. Pat. Nos. 5,669,894 and 6,849,665. When a covering layer 340 is used, materials suitable for use as a backsheet 362 are also suitable for use as covering layer 340. A particularly preferred material for use as removable distribution layer 320 is a web comprising the non-biopersistent vitreous microfibers that are described in detail below.

While removable/replaceable core component 310 is shown in FIG. 3A as being positioned between backsheet 362 and fixed distribution member 351, it should be recognized that removable/replaceable core component 310 may also be positioned between fixed distribution member 351 and acquisition member 352. In an alternative embodiment (not shown), diaper 300 is provided with first and second fixed distribution members and removable/replaceable core component is provided with opposed liquid transfer regions and is positioned between the two fixed distribution members.

In yet another alternative embodiment (not shown), the entire absorbent core is removable/replaceable with no fixed core members present.

Such embodiments having removable/replaceable components are described more fully in one or more of the following: U.S. Pat. Nos. 6,989,005, 6,989,006, 6,932,800 and U.S. patent application Ser. No. 11/099791 filed in the name of Lavon, et al. on Apr.4, 2005 and in U.S. Pat. Application Publications 2003/0199844, 2004/0024379, 2004/0030314.

III. Fluid Distribution Member Material

A suitable microfiber for use as a fluid distribution member for the various embodiments of the present invention is a non-biopersistent inorganic vitreous microfiber having an average effective diameter of between about 0.1 microns and 6 microns. For purposes of the present invention, an inorganic vitreous microfiber is non-biopersistent if its in vitro dissolution rate, $k_{dis}$, is equal to or greater than 100 ng/cm$^2$/hr when measured according to the test method described below. Preferably the non-biopersistent inorganic vitreous microfibers useful in the present invention have dissolution rates, $k_{dis}$, of more than about 125 ng/cm$^2$/hr, more preferably more than about 150 ng/cm$^2$/hr, and even more preferably more than about 250 ng/cm$^2$/hr. It has been found that such microfibers have the particularly desirable combination of fluid handling properties, resiliency, softness and lack of biopersistence. Inorganic compositions suitable for making microfibers useful in the present invention are described in European Pat. 1 048 625B, U.S. Pat. No. 6,261,335 and U.S. Pat. Application Publication 2003/0015003. Suitable non-biopersistent inorganic vitreous microfibers are available from Lauscha Fiber International Corp. of Summerville, S.C.

Such inorganic vitreous microfibers may be produced using known techniques including:
1. the centrifugal or "rotary" process where molten glass enters a centrifugal spinner from a glass melting furnace and rotation thereof causes relatively large diameter glass strands to stream from orifices located in the spinner's periphery which are then further thinned by stretching caused by high velocity hot air (described, for example, in U.S. Pat. Nos. 4,767,431 and 5,554,324), and
2. the flame attenuation process where molten glass streams are extruded from the bottom of a melting pot to form fibers which are then engaged by a series of feed rolls and attenuated into fine fibers by a blast of hot gas having a temperature greater than the softening point of the glass and a velocity great enough to cause such attenuation (described, for example, in U.S. Pat. No. 2,571,025).

While all known web forming techniques that are suitable for staple fibers may be used with a vitreous microfiber staple feedstock, wet laying is particularly preferred as a means to produce a web form of the vitreous microfibers. As is well known the vitreous microfiber staple is dispersed in an aqueous medium; the dispersion is then laid down on a forming screen from a headbox or other suitable distribution means; the aqueous medium drains through the forming screen to form a nascent web which is then dried and wound to form a roll of vitreous microfibers.

In an alternative embodiment the web is provided with a binder so as to provide increased mechanical stability thereto. Nonlimiting examples of such binders include:
Thermoplastic binder fibers or powder added to the furnish when the vitreous microfibers are wet laid. The drying step can then be used to melt the binder fibers so as to stabilize the web. Desirably, the binder fibers comprise a hydrophilic material. Such binder fibers can comprise only a single thermoplastic material or they may comprise a bicomponent fiber comprising two thermoplastic materials where one of the materials has a melting point substantially higher than the other of the materials so as to preserve fiber integrity when the fiber is exposed to a temperature that causes flow of the lower melting material. Alternatively, thermoplastic binder powders as are known to the art are also suitable.
Application of a binder material to the web either as a component of the furnish or after web formation. This application could be a latex binder applied to the wet nascent web and then cured in the drying step; a spray of a polymeric solution (e.g., aqueous polyvinyl alcohol) which is dried along with the fibers in the drying step; or a spray of a binding adhesive (e.g., a hot melt material) to the dried web before it is wound.
Application of thermosetting wet strength resins known to the papermaking arts either as a component of the furnish or after web formation. For example, a spray application of KYMENE 557H as is available from Hercules, Inc. of Wilmington, Del. has been found to increase the strength of a vitreous fibrous assembly.
If a low level of cellulosic fiber (e.g., eucalyptus fibers or crill) is used, additional wet strength materials known to the papermaking arts may also be used to stabilize the web (again either applied as a furnish component or after web formation). Nonlimiting examples of such materials include and PAREZ 631 NC as is available from Lanxess Corporation of Pittsburgh, Pa. and the aforementioned KYMENE 557H.

Since such binders may affect the fluid handling properties of the web, only the minimum level necessary for the required mechanical strength should be used. For thermoplastic binders the level is preferably less than about 20%, more preferably less than about 15%. For post formation binders the add-on to the dry web is preferably less than about 20%, more preferably less than about 15%.

In addition to blends with binder fibers the other types of fibers may be incorporated into the distribution member. For example:
In some instances it may also be desirable for the fibrous assembly to comprise a proportion of other fibers. Such fibers may provide bonding sites for a permanent wet strength means so as to enhance mechanical stability of the final web. Suitable high surface area fibers include microfibrous cellulose, high surface area cellulosic fibers (e.g., conventional cellulosic pulp fibers, particularly eucalyptus fibers), and highly refined cellulosic fibers (preferably with Canadian Standard Freeness of less than about 200, more preferably from about 40 to about 100) referred to herein as "crill".
It may also be desirable for a portion of the fibers in the web to comprise synthetic polymeric or semi-synthetic polymeric fibers. For example, synthetic fibers such as polyester, polypropylene, or polyethylene may be used in relatively small amounts to provide additional strength to the structure. Also suitable are semi-synthetic fibers such as rayon. One suitable synthetic fibrous material is a short staple (3-18 mm) polypropylene fiber having a length suitable for wet laying marketed by FiberVisions of Covington, Ga. as CREATE-WL.

The concentration of such fibers depends on the desired final properties of the web. Suitably such fibers are used at a level less than about 15%, preferably less than about 10%.

In an alternate embodiment, the web may be airlaid directly after formation of the microfibers by collecting the fibers on a suitable forming device or by using conventional airlaying techniques using staple-length fibers. In either case, the web in this embodiment may be formed by collection of fibers on a foraminous structure. In preferred processes of this type a vacuum system underlying the foraminous structure can aid in gathering the fibers into a web form. Airlaid webs of this type can also use binders and other fibrous materials as described above for wet-laid webs.

Suitably, the web has a basis weight of between about 40 g/m$^2$ and about 350 g/m$^2$, preferably between about 80 g/m$^2$ and about 160 g/m$^2$. Layers of the web may be stacked to achieve higher overall basis weights. The density of the web is suitably between about 0.04 g/cc and about 0.25 g/cc, preferably between about 0.07 g/cc and about 0.10 g/cc.

IV. Important Attributes of the Fluid Distribution Members

Tensile Strength

As will be recognized, mechanical integrity of the material comprising the fluid distribution members of the present invention is important for both reliability in the process used to produce the member and for reliable performance of any product incorporating the member. One measure of mechanical integrity is dry tensile strength (a method is provided in the Test methods section below). Typically, a material for use as a fluid distribution member according to the present invention has a dry tensile strength of at least about 0.05 kN/m, preferably at least about 0.25 kN/m, more preferably at least about 0.4 kN/m or even greater when measured according to the method described in the Test methods section below.

Fluid Handling

The primary functions of the fluid distribution member are to dewater any acquisition members in the absorbent article that are in capillary communication therewith and to distribute fluid as rapidly as possible throughout the distribution member. In order to spontaneously dewater an acquisition member via a capillary mechanism to achieve to a particular moisture content in the acquisition member, the absorptive capillary pressure of the distribution member must be equal to or greater than the desorptive capillary pressure of the acquisition layer at that particular moisture content. It is desirable for the distribution member to have sufficient additional absorptive capillary pressure to enable wicking of fluid throughout the distribution member, often against gravity.

Surprisingly, very high absorptive capillary pressure is not necessarily advantageous in a fluid distribution member. In part, this is due to the fact that capillary continuity within an acquisition member is lost below a certain moisture content. When the moisture content of the acquisition member is below this level, increasing the absorptive capillary pressure of an adjacent member does not necessarily result in further capillary dewatering of the acquisition member. Another reason very high absorptive capillary pressure is not necessarily advantageous in a fluid distribution member is that the small pore sizes necessary to achieve high capillary pressures also tend to result in the member having relatively low permeability and a low rate of wicking.

For purposes of the present invention, these capillary forces are measured in terms of the member's ability to wick fluid to a specific height against gravity as described in the various fluid handling tests discussed below.

A. Vertical Wicking Rate of the Distribution Member

The rate at which the fluid distribution member wicks fluid is determined, amongst other factors, by the capillary pressure and the permeability of the structure. For purposes of the present disclosure the wicking rate is determined by measuring the time taken for a colored test liquid (e.g., synthetic urine) in a reservoir to wick a specified vertical distance through a representative sample of the member according to the Vertical Wicking Rate test described in the Test methods section below.

The fluid distribution members of the present invention comprises a material that suitably wicks fluid vertically to a height of 5 cm in less than about 5 minutes, preferably in less than about 2 minutes, more preferably in less than about 1 minute, and even more preferably in less than about 30 seconds. Preferred embodiments of the fluid distribution members of the present invention comprise a material that suitably wicks fluid vertically to a height of 10 cm in less than about 15 minutes, preferably in less than about 10 minutes, more preferably in less than about 5 minutes, and even more preferably in less than about 2.5 minutes. Particularly preferred embodiments the fluid distribution members of the present invention comprise a material that suitably wicks fluid vertically to a height of 15 cm in less than about 20 minutes, preferably in less than about 15 minutes, more preferably in less than about 10 minutes, and even more preferably in less than about 5.5 minutes.

B. Vertical Wicking Height

For purposes of the present invention, the capillary absorption pressure of a porous material is determined by measuring its ability to wick fluid vertically, according to the Vertical Wicking Height test described in the Test methods section below.

The fluid distribution members of the present invention preferably, but not necessarily, have vertical wicking heights of from about 15 cm to about 90 cm, more preferably from about 20 cm to about 80 cm, and even more preferably from about 25 cm to about 70 cm.

C. Permeability of the Distribution Member to Fluid

For purposes of the present disclosure the permeability of the fluid distribution member is measured according to the Permeability test described in the Test methods section below.

Desirably, a fluid distribution member of the present invention comprises a material having as high a permeability as possible consistent with other fluid handling properties, even greater than 100 Darcys. Suitably, permeability should be greater than about 4 Darcys, preferably greater than about 10 Darcys. Typically, the fluid distribution members of the present invention have permeability values of from about 10 Darcys to about 35 Darcys, more typically from about 15 Darcys to about 30 Darcys, and even more typically from about 15 Darcys to about 25 Darcys.

D. Surface Tension Reduction

As noted above, surfactant materials are frequently added to absorbent article components to improve the hydrophilicity of a variety of materials therein. The presence of surfactants can cause the surface tension of absorbed fluids to be reduced substantially. Desirably, the distribution members of the present invention comprise vitreous microfibers which are inherently hydrophilic. As a result, no surfactant is needed to cause them to become hydrophilic.

In one embodiment of the present invention, the distribution member has a surface tension reduction of less than about 10 mN/m, when tested in accordance with the Surface Tension Reduction Test in the Test methods section. Preferably, the surface tension reduction is less than about 8 mN/m, more preferably less than about 5 mN/m, and most preferably less than about 2 mN/m.

E. Biopersistence

As noted above, distribution members of the present invention comprise inorganic vitreous microfibers which are considered to be non-biopersistent.

V. Test Methods

The following is a detailed description of the various methods used to characterize the distribution materials of the present invention. It will be recognized that, with respect to test methods A, B and C, where the test material lacks sufficient integrity to withstand the testing protocol, a hydrophobic screen that does not impact wicking performance can be used to support the material.

Sample Preparation

Before using any of the following test methods to evaluate a material, the material should be prepared for evaluation according to at least one of the following steps.

Where the material to be tested is obtained from an absorbent article, sufficient number of representative absorbent articles should be selected from the retail packaging of the absorbent article to conduct all required tests. Each article should be disassembled in a manner that minimally disturbs the structure of any layers comprising the absorbent article. For example, adhesively joined layers can be separated by first freezing them using a freeze spray such as Freez-It® as is available from ITW Chemtronics Americas of Kennesaw, Ga.

All samples should be preconditioned at 22±2° C. and 50±2% relative humidity prior to evaluation using any of the following test methods unless specified otherwise. All tests are conducted at 22±2° C. and 50±2% relative humidity unless specified otherwise.

A. Vertical Wicking Rate

A rectilinear test strip of material 1-2 cm wide and approximately 20 cm long is cut taking care not to compress the material or otherwise unduly disturb its structure. The orientation of the material should be such that the long dimension of the sample corresponds with the primary direction in which fluid is transported through the material in an absorbent article. The strip is suspended vertically from a suitable adjustable support such that the material is not excessively curled, twisted, creased or wrinkled, and the lower edge of the material is approximately 2 cm above the rim of a Petri dish having a diameter of at least 6 cm. The Petri dish is filled to a depth of at least 1 cm with a 0.9% solution of sodium chloride. Approximately 0.25 g/l F&DC Blue No. 1 colorant powder is added to the solution to impart an intense uniform blue color. A ruler graduated in millimeters is clamped vertically by suitable means such that the ruler is alongside but not touching the test strip and the zero millimeter mark is at the surface of the liquid. The test strip is lowered rapidly so that the bottom 5 mm of the strip is submerged in the liquid near the center of the Petri dish. A stopwatch is activated as soon as the bottom of the test strip is submerged in the liquid. The time taken for the fluid front to wick to 5 cm, 10 cm and 15 cm is recorded by visual inspection of the test strip and ruler. The highest point to which fluid has wicked is considered to be the fluid front. Measurements are conducted in triplicate and the average value is used to represent the wicking rate at the specified height.

B. Vertical Wicking Height

A rectilinear test strip of material 1-2 cm wide is cut taking care not to compress the material or otherwise unduly disturb its structure. The length of the sample is at least several centimeters longer than the expected vertical wicking height of the material. The orientation of the material should be such that the long dimension of the sample corresponds with the primary direction in which fluid is transported through the material in an absorbent article. The strip is suspended vertically from a suitable support within a rigid clear impervious cylinder having an internal diameter of approximately 3-4 cm, and an outer diameter which will fit through the neck of a 2 liter Ehrlenmeyer flask. The cylinder is clamped in a vertical position, such that the test strip protrudes approximately 0.5 cm from the bottom of the cylinder. The strip is not unduly curled, twisted, creased or wrinkled, and does not touch the inner walls of the cylinder. The top of the cylinder is sealed except for a pinhole. A 2 liter Ehrlenmeyer flask containing 1 liter of a 0.9% solution of sodium chloride by weight is positioned directly below the bottom of the cylinder. Approximately 0.25 g/l F&DC Blue No. 1 colorant powder is added to the solution to impart an intense uniform blue color. The cylinder is lowered through the neck of the Ehrlenmeyer flask until the bottom 5 mm of the cylinder is submerged in the liquid. The height of the fluid front above the surface of the liquid in the Ehrlenmeyer flask is measured by any suitable means, such as pre-inscribed gradations on the cylinder, or with the aid of a suitable ruler. The highest point to which fluid has wicked is considered to be the fluid front. For purposes of the present invention vertical wicking height is measured at 16 hours±30 minutes. Measurements are conducted in triplicate and the average value is used to represent the wicking height of the material.

C. Permeability

Sample

A rectilinear test strip of material approximately 2.5 cm wide and approximately 30 cm long is cut taking care not to compress the material or otherwise unduly disturb its structure. The orientation of the material should be such that the long dimension of the sample corresponds with the primary direction in which fluid is transported through the material in an absorbent article. The thickness of the sample is determined as described below. The width of the test strip is measured to within ±0.5 mm. The cross-sectional area (A) of the test strip is determined by multiplying the thickness of the strip by its width.

Apparatus and Test Setup

Figure 5:
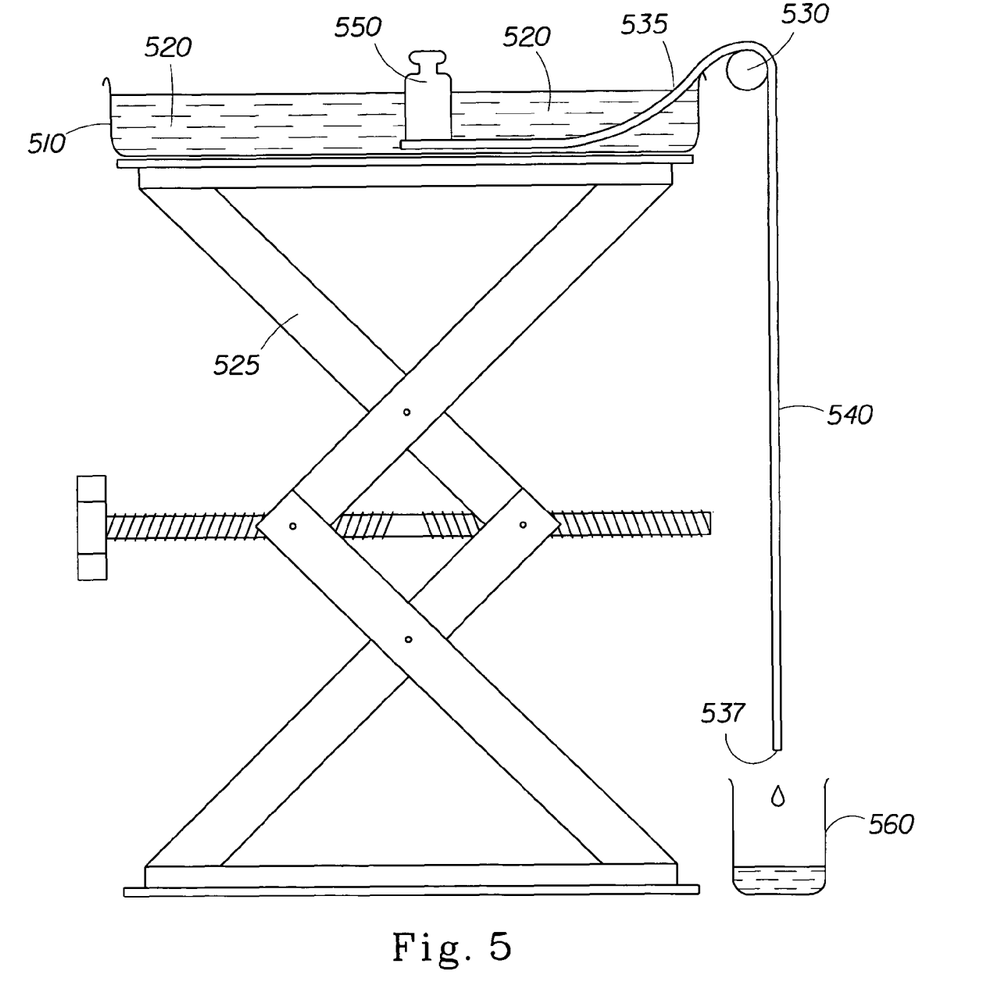
FIG. 5 is a diagrammatic view of an apparatus suitable for measurement of permeability.

A suitable apparatus 500 is shown in FIG. 5. A glass baking dish 510 approximately 20 cm long, 20 cm wide and 5 cm deep is filled to a depth of approximately 4 cm with distilled water 520. The dish 510 is supported on a suitable stand 525 in a sealable chamber (not shown) with a transparent (e.g., LEXAN) panel and with approximate internal dimensions 45 cm×45 cm×40 cm (height×width×depth). The dish 510 is situated such that the fluid is of uniform depth in the dish and the surface of the fluid is approximately 30 cm above the floor of the chamber. A cylindrical plastic (e.g., LEXAN) support bar 530 with a diameter of 2 cm is clamped parallel to one edge of the dish with the central axis of the bar 530 at the same height as the rim of the dish and 2 cm from the outer edge of the rim. The chamber is sealed and allowed to stand at 22±2° C. for at least two hours to allow the humidity in the chamber to increase thereby minimizing the rate of evaporation of the fluid within the chamber. The test strip 540 is saturated with water by submerging it in a dish of distilled water for approximately 1 minute. The saturated test strip 540 is then carefully removed from the water and placed in the chamber such that approximately 5 cm of the test strip 540 is submerged in the fluid 520. The remainder of the strip 540 is draped over the plastic support bar 530 and allowed to hang vertically over a 100 ml beaker 560 such that there are no sharp bends or kinks in the strip. If necessary, a weight 550 sufficient to prevent slippage of test strip 540 (typically 100 g is sufficient) is placed on the end of the submerged portion to anchor the strip 540.

Operation

The chamber is sealed and the water is allowed to wick through the sample and drip into the beaker for thirty minutes. The chamber is then opened; the beaker is replaced with a clean, dry beaker of known weight ($W_i$); and a stopwatch is activated simultaneously. The chamber is re-sealed immediately and water is allowed to drip into the beaker for approximately 20 minutes. The chamber is opened and the beaker is promptly replaced by another clean, dry beaker of known weight, after which the chamber is resealed immediately. The time period during which water was collected in the beaker just removed is recorded (t). This beaker containing the collected water is weighed immediately upon removal from the chamber and the weight recorded ($W_f$). Water is collected in three separate beakers successively in this fashion, with the initial weight, final weight, and collection time recorded for each beaker. After the third beaker has been removed from the chamber, the absolute vertical distance (Δh) between the surface 535 of the water and the end of the test strip 537 is measured. The strip is marked on one edge with a waterproof marker or other suitable means at the surface of the water. The test strip is then carefully removed and laid on a flat surface. The length of the portion of the strip which was not submerged (L) is determined by measuring the distance from the end of the strip 537 to the mark made at the surface of the water.

Calculation and Reporting

The volumetric flow rate for each beaker of fluid collected is calculated using the following equation:

$$Q_n = \frac{(W_f - W_i) \times VS_w}{t}$$

where: $Q_n$ is the volumetric flow rate [in m³/s]
$W_f$ is the final weight of the beaker [in grams]
$W_i$ is the initial weight of the beaker [in grams]
$VS_w$ is the specific volume of water [in m³/g] (i. e., 1.00× 10⁻⁶ m³/g), and
t is the time of fluid collection in the beaker [in seconds].

The average volumetric flow rate, Q, is the arithmetic average of the three values obtained in this fashion.

The permeability of the material is calculated using the following equation:

$$k = \frac{Q \times L \times \mu}{A \times \Delta h \times \rho \times g}$$

Where k is the permeability of the material [in m²],

Q is the average volumetric flow rate [in m³/s],

L is the length of the test strip which was not submerged [in m], $\mu$ is the absolute viscosity of water [in N·s/m² (or kg/m·s)] (i.e., 0.001 kg/m·s), A is the cross-sectional area of the sample [in m²], $\Delta h$ is the vertical distance between the surface of the fluid in the dish and the lower end of the test strip [in m], $\rho$ is the density of the fluid [in kg/m³] (i.e., 1000 kg/m³), and g is the acceleration due to gravity [in m/s²]. (i.e., 9.80 m/s²)

The permeability of the material, k, is obtained in Darcys by dividing the value of k in m² by 9.87×10⁻¹³ m²/Darcy.

D. Surface Tension Reduction

A blank solution is prepared by filtering 100 ml of a 0.9% sodium chloride solution through a Whatman No. 41 filter paper and collecting the filtrate in a 150 ml beaker. A representative sample of the material weighing 3.0±0.01 grams is placed in a 1 liter beaker containing 100 ml of a 0.9% sodium chloride solution. The material is submerged in the liquid and agitated gently with the aid of a glass rod for a period of 1 minute. The contents of the beaker are filtered through a Whatman No. 41 filter paper and the filtrate is collected in a 150 ml beaker. The material remaining in the filter paper is pressed gently with the glass rod to express absorbed fluid if insufficient filtrate is obtained initially for measurement of its surface tension. The surface tension of the blank and of the filtrate is measured using a Surface Tensiomat Model 21 available from Fisher Scientific, a K10 Tensiometer available from Kriiss GmbH, Germany, or equivalent surface tensiometer. The tensiometer is set up according to the manufacturer's instructions and calibrated using distilled water, acetone, and a 5% solution of acetone in water. The surface tension values for these liquids are 72±1.5 mN/m, 23±1.5 mN/m, and 55±1.5 mN/m, respectively. A correction factor is applied where necessary as indicated by the manufacturer's instructions. After calibrating the instrument, the surface tensions of the 0.9% sodium chloride solution and the filtrate are determined in the same fashion. The duNuoy ring or equivalent is thoroughly cleaned between measurements e.g., by heating in a Bunsen flame. Surface tension reduction is defined as the difference between the surface tension of the blank and the surface tension of the filtrate.

E. Biopersistence

For purposes of the present invention, an inorganic vitreous microfiber is non-biopersistent if its in vitro dissolution rate, $k_{dis}$, is equal to or greater than 100 ng/cm²/hr when measured according to the test method described by Russell M. Potter in *Glastechnische Berichte* 43, 46-55 (2000).

F. Average Effective Fiber Diameter

The average effective fiber diameter is determined by measuring the surface area of a sample of known mass of the fibers by a BET technique. The average effective fiber diameter is calculated using the formula:

$$d = \frac{4}{\rho \times SSA}$$

where d is the average effective fiber diameter, SSA is the surface area per gram of the fibers as determined from the BET measurement, and $\rho$ is the density of the bulk glass from which the fibers are made and is typically 2.6 g/cc (2.6×10⁶ g/m³).

G. Tensile Strength

The method for measuring tensile strength is based on TAPPI (Technical Association of the Pulp and Paper industries) Method T 494 om-96. A rectilinear test strip of material 25.4±1 mm wide and approximately 15 cm long is cut taking care not to compress the material or otherwise unduly disturb its structure. The orientation of the material should be such that the long dimension of the sample corresponds with the machine direction of the web from which the sample is cut. The thickness of the material is determined as described below. The test strip should be free from abnormalities, creases or wrinkles.

The test specimen is mounted in a calibrated constant-rate-of-elongation type tensile tester with an initial test span of 100 mm. Suitable instruments include the MTS Synergie 200/L and the MTS Alliance RT/1 available from MTS of Cary, N.C. The test instrument meets the following requirements:

Two clamping jaws, each with a line contact for gripping the specimen, with the line of contact perpendicular to the direction of the applied load and with means for controlling and adjusting the clamping pressure.

The clamping surfaces of the two jaws are in the same plane and so aligned that they hold the specimen in that plane throughout the test.

The distance between the line contacts at the start of the test is adjustable to within ±0.5 mm for the initial specified test span.

The rate of separation of the jaws is set to 25±5 mm/min.

A load cell with a dynamic range such that the measured peak force is within the dynamic range of the load cell.

A suitable recorder for recording the maximum tensile stress before rupture of the specimen.

The specimen is mounted by aligning and clamping it first in one jaw, carefully removing any slack, and aligning and clamping it in the second jaw. A clamping pressure is used so that neither slippage nor damage to the specimen occurs. Ten specimens are tested and the average breaking force is calculated. Data are rejected where the test specimen slips in the jaws, breaks in the clamping area, or shows evidence of uneven stretching across its width. Further, data are rejected where the specimen breaks within 5 mm of the clamp area if further inspection indicates that the break location is due to improper clamping conditions or misalignment. The average tensile strength is obtained by dividing the average breaking force by the specimen width, and is reported in kN/m.

H. Basis Weight

A representative piece of the material is cut with clean edges such that the area covered by the material can be measured to at least 3 significant figures. The piece of material is then weighed on a balance to at least 3 significant figures. The basis weight is calculated by dividing the area of the material by its weight and is reported in grams per square meter ($g/m^2$).

I. Thickness

The thickness of a material is measured using a dial gauge or digital equivalent with a resolution of ±1 µm and a circular "foot" having a flat bottom surface with an area of approximately 6.5 $cm^2$. The gauge is mounted over a base having a horizontal flat rigid upper surface, such that the entire bottom surface of the foot contacts the upper surface of the base. The force exerted by the foot on the base or on a material inserted between the foot and the base is approximately 0.4 N (41 $g_f$) and is independent of the thickness of the material. The force exerted by the foot of the gauge can be measured by mounting the gauge over a suitable top-loading balance such that the balance pan is in the same relative position to the gauge as the base. The force is adjusted by adding weight to the foot such that the pressure exerted by the foot is 600±10 Pa.

The thickness of the material is determined by reading the gauge with the foot resting on the base ($G_0$). The foot of the gauge is then raised and the material is laid flat on the base. The foot is lowered gently onto the material & the gauge reading taken 5 seconds after complete release of the foot ($G_T$). The thickness of the material at that location is the difference between the two readings ($G_T$–$G_0$). Several readings are taken at random locations on the sample in this fashion and the results averaged to determine the thickness of the material.

J. Density

The weight, area and thickness of a representative sample of the material are measured according to the Basis Weight and Thickness methods described above. The area is multiplied by the thickness to obtain the volume of the sample. The density is determined by dividing the weight of the sample by its volume and is reported in $kg/m^3$.

VI. REPRESENTATIVE EXAMPLES

Example 1

A composition comprising 62 parts $SiO_2$, 3 parts $Al_2O_3$, 7 parts CaO, 4 parts MgO, 17 parts $Na_2O+K_2O$, and 7 parts $B_2O_3$, is heated until molten, and formed into vitreous microfibers using the centrifugal or "rotary" process described above. A flame attenuation process is used to form microfibers comprising the same chemical composition. Portions of the fibers from each process are blended to provide a mixture having an average effective fiber diameter of 1.8 µm, using a density of 2.6 g/cc for the bulk composition. The fibers are converted into a web without binder via a wet-laying process as described above. The basis weight of the web is 120 $g/m^2$, and the thickness is 1.13 mm. The density is calculated to be 0.106 g/cc. The fibers are determined to be non-biopersistent. The web comprising non-biopersistent inorganic vitreous fibers has a tensile strength of 0.44 kN/m, a vertical wicking height of 64 cm, and a permeability of 21 Darcys. The material wicks fluid to 5 cm within 30 seconds; to 10 cm within 150 seconds, and to 15 cm within 330 seconds. A piece of the web is used as a component of a distribution member in an infant diaper. A piece of the web is used as a component of a distribution member in a removable core in a second diaper.

Example 2

A composition comprising 62 parts $SiO_2$, 3 parts $Al_2O_3$, 7 parts CaO, 4 parts MgO, 17 parts $Na_2O+K_2O$, and 7 parts $B_2O_3$, is heated until molten, and formed into vitreous microfibers using the centrifugal or "rotary" process described above. The average effective fiber diameter is determined to be 1.8 µm, using a density of 2.6 g/cc for the bulk composition. The fibers are collected and converted into a web without binder via an air-laying process as described above. The basis weight of the web is 120 $g/m^2$, and the thickness is 2.5 mm measured under a pressure of 600 Pa. The density is calculated to be 0.048 g/cc. The fibers are determined to be non-biopersistent. The web comprising non-biopersistent inorganic vitreous fibers wicks a 0.9% saline solution to a height of 5 cm within 1 minute and to a height of 10 cm within 5 minutes. The material has a permeability of 20 Darcys. A piece of the web is used as a component of a fixed distribution member of a diaper with a removable core.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 m".

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising
    a fluid permeable topsheet,
    an opposed backsheet, and
    an absorbent core disposed between said topsheet and said backsheet and having a crotch region, a front waist region, and a rear waist region, said absorbent core comprising an absorbent storage member comprising
        a superabsorbent polymer and
        a fluid distribution member comprising an assembly of hydrophilic, non-biopersistent inorganic vitreous microfibers having an in vitro dissolution rate of equal to or greater than 150 $ng/cm^2/hr$, wherein said fluid distribution member has a surface tension reduction of less than about 10 mN/m;
    wherein said microfibers have an average effective diameter of from about 0.1 micron to about 6 microns and an aspect ratio of at least about 100, wherein said aspect ratio of said microfibers is the contour length of said microfibers divided by the average effective diameter of said microfibers.

2. The absorbent article according to claim 1 wherein:
a) said assembly has a basis weight between about 40 g/m$^2$ and about 350 g/m$^2$;
b) said assembly has a density between about 0.04 g/cm$^3$ and about 0.25 g/cm$^3$; and
c) said inorganic vitreous microfibers have an average effective diameter between about 0.1 micron and about 6 microns.

3. The absorbent article according to claim 1 wherein said assembly of said non-biopersistent inorganic vitreous microfibers further comprises a binder selected from the group consisting of thermoplastic binder fibers, thermoplastic powders, latex binders, binding adhesives, thermosetting wet strength resins, papermaking wet strength materials and mixtures thereof.

4. The absorbent article according to claim 1 wherein said core is a multi-component core and comprises a non-removable core component and a removable/replaceable core component, said removable/replaceable core component comprising the fluid distribution member.

5. The absorbent article according to claim 4 wherein said fluid distribution member vertically wicks a 0.9% saline solution to a height of 5 cm in less than about 5 minutes.

6. The absorbent article according to claim 4 wherein said fluid distribution member vertically wicks a 0.9% saline solution to a height of 5 cm in less than about 2 minutes.

7. The absorbent article according to claim 4 wherein said fluid distribution member vertically wicks a 0.9% saline solution to a height of 5 cm in less than about 1 minute.

8. The absorbent article according to claim 4 wherein said fluid distribution member has a 16 hour vertical wicking height for a 0.9% saline solution of between about 15 cm and about 90 cm.

9. The absorbent article according to claim 4 wherein said fluid distribution member has a permeability greater than about 4 Darcys.

10. The absorbent article according to claim 9 wherein said permeability is greater than about 100 Darcys.

11. The absorbent article according to claim 9 wherein said permeability is between about 10 Darcys and about 35 Darcys.

12. The absorbent article according to claim 1 wherein said in vitro dissolution rate is equal to or greater than 250 ng/cm$^2$/hr.

13. A disposable absorbent article comprising
a fluid permeable topsheet,
an opposed backsheet, and
an absorbent core disposed between said topsheet and said backsheet and having a crotch region a front waist region and a rear waist region, said absorbent core comprising a superabsorbent polymer and
a removable/replaceable core component comprising a fluid distribution member comprising hydrophilic, non-biopersistent inorganic vitreous microfibers;
wherein said fluid distribution member has a surface tension reduction of less than about 10 mN/m;
wherein said microfibers have an average effective diameter of from about 0.1 micron to about 6 microns and an aspect ratio of at least about 100 , wherein said aspect ratio of said microfibers is the contour length of said microfibers divided by the average effective diameter of said microfibers.

14. The absorbent article according to claim 13 wherein said non-biopersistent inorganic vitreous microfibers have an in vitro dissolution rate of equal to or greater than 150 ng/cm$^2$/hr.

15. The absorbent article according to claim 13 wherein said non-biopersistent inorganic vitreous microfibers have an in vitro dissolution rate of equal to or greater than 250 ng/cm$^2$/hr.

\* \* \* \* \*